US012521267B2

(12) United States Patent
Kim

(10) Patent No.: US 12,521,267 B2
(45) Date of Patent: Jan. 13, 2026

(54) INGROWN FINGERNAIL/TOENAIL CORRECTION DEVICE USING SHAPE MEMORY ALLOY

(71) Applicant: THE CATHOLIC UNIVERSITY OF KOREA INDUSTRY-ACADEMIC COOPERATION FOUNDATION, Seoul (KR)

(72) Inventor: Yeong Ho Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 128 days.

(21) Appl. No.: 18/681,687

(22) PCT Filed: Oct. 13, 2022

(86) PCT No.: PCT/KR2022/015497

§ 371 (c)(1),
(2) Date: Feb. 6, 2024

(87) PCT Pub. No.: WO2023/068652

PCT Pub. Date: Apr. 27, 2023

(65) Prior Publication Data

US 2024/0341993 A1 Oct. 17, 2024

(30) Foreign Application Priority Data

Oct. 20, 2021 (KR) ........................ 10-2021-0139868

(51) Int. Cl.
*A61F 5/11* (2006.01)

(52) U.S. Cl.
CPC ...................................... *A61F 5/11* (2013.01)

(58) Field of Classification Search
CPC .......... A61F 13/064; A61F 2013/00404; A61F 5/019; A61F 13/063; A61F 13/069; A61F 5/0102; A61F 5/0585; A61F 5/11; A61F 5/0111; A61F 5/0116; A61F 5/058; A43B 3/102; A43B 5/12; A43B 7/1445; A43B 7/1425; A43B 7/1435
See application file for complete search history.

(56) References Cited

FOREIGN PATENT DOCUMENTS

| | | | |
|---|---|---|---|
| JP | 08-215227 | A | 8/1996 |
| JP | 2007-312911 | A | 12/2007 |
| JP | 6147804 | B2 * | 6/2017 |
| KR | 10-0756079 | B1 | 9/2007 |
| KR | 10-0962457 | B1 | 6/2010 |
| KR | 20-0471630 | Y1 | 3/2014 |
| KR | 10-1565692 | B1 | 11/2015 |

* cited by examiner

*Primary Examiner* — Ophelia A Hawthorne
(74) *Attorney, Agent, or Firm* — Bridgeway IP Law Group, PLLC; Jihun Kim

(57) ABSTRACT

An ingrown fingernail/toenail correction device using a shape memory alloy, includes a first fixing part configured to be fixed to an ingrown fingernail/toenail, a second fixing part configured to be fixed to the ingrown fingernail/toenail and spaced apart from the first fixing part at a predetermined distance, and a correction part inserted into the first fixing part and the second fixing part and made of a shape memory alloy so that when the correction part reaches a preset temperature, a shape of the correction part returns to a preset shape to provide a corrective force to the first fixing part and the second fixing part.

14 Claims, 9 Drawing Sheets

INGROWN FINGERNAIL/TOENAIL CORRECTION DEVICE USING SHAPE MEMORY ALLOY

TECHNICAL FIELD

The present invention relates to an ingrown fingernail/toenail correction device using a shape memory alloy, and more particularly, to an ingrown fingernail/toenail correction device using a shape memory alloy, which is capable of effectively correcting an ingrown fingernail/toenail.

BACKGROUND ART

[Research and development project that supported the invention]
[Project Number] ZC20DISI0537
[Department] Seoul St. Mary's Hospital, Catholic University of Korea
[Project Name] 2020 Emerging Research Support Program
[Project Title] New ingrown fingernail/toenail correction device using shape memory alloy and 3D printer
[Contribution Rate] 100%
[Lead Sponsor] Seoul St. Mary's Hospital, Catholic University of Korea
[Investigator] Youngho Kim Like the foundation of a building, the feet are the most important parts for maintaining the balance of the body. It is necessary to preferentially maintain the balance of the feet in a neutral position in order to maintain the overall balance of the body. In particular, the big toe is a very important body part for walking and posture because the big toe supports 25% of the pressure of the entire foot.

However, an ingrown toenail symptom, in which the big toe or little toe digs into the flesh, is caused by various factors, such as wearing high heels or pointed-toe shoes over a long period of time, frequent strenuous exercise, wearing severely tight shoes over a long period of time, deeply trimmed outer portions of toenails, deformation in shape of the toenail with athlete's foot left unattended over a long period of time, and naturally and severely curved toenails due to obesity or aging. The ingrown toenail becomes redder and more swollen over time, and the area around the toenail begins to fester, which causes excruciating pain that can lead to walking difficulty.

In the related art, there are known methods for treating the ingrown toenail, such as a surgical procedure of removing the root of the ingrown toenail and a method using correction tools or devices. However, the surgical procedure has the disadvantage of causing significant pain and a long therapeutic period. The ingrown toenail correction device in the related art is disadvantageous in that the patient cannot autonomously and easily use the ingrown toenail correction device, the patient suffers from significant pain even though anesthesia is performed during a hospital procedure by a practitioner, and the procedure using the ingrown toenail correction device is expensive and cumbersome.

(Patent Document 1) Korean Patent No. 10-1565692 (Oct. 28, 2015)

(Utility Model Document 1) Korean Utility Model Registration No. 20-0471630 (Feb. 27, 2014)

DISCLOSURE

Technical Problem

The present invention has been made in an effort to solve the above-mentioned problem, and an object of the present invention is to provide an ingrown fingernail/toenail correction device using a shape memory alloy, which is configured to correct an ingrown fingernail/toenail by inserting at least one correction part, which is made of a shape memory alloy, into a plurality of fixing parts and then attaching the correction part to the ingrown fingernail/toenail.

Technical problems to be solved by the present invention are not limited to the above-mentioned technical problems, and other technical problems, which are not mentioned above, may be clearly understood from the following descriptions by those skilled in the art to which the present invention pertains.

Technical Solution

In order to achieve the above-mentioned object, the present invention provides an ingrown fingernail/toenail correction device using a shape memory alloy, the ingrown fingernail/toenail correction device including: a first fixing part configured to be fixed to an ingrown fingernail/toenail; a second fixing part configured to be fixed to the ingrown fingernail/toenail and spaced apart from the first fixing part at a predetermined distance; and a correction part inserted into the first fixing part and the second fixing part and made of a shape memory alloy so that when the correction part reaches a preset temperature, a shape of the correction part returns to a preset shape to provide a corrective force to the first fixing part and the second fixing part.

In the embodiment of the present invention, the first fixing part may include: a first attachment portion configured to be attached to one side of an upper surface of the ingrown fingernail/toenail; and a first central support portion formed at a center of an upper surface of the first attachment portion, and one side portion of the correction part may be fixedly inserted into the first central support portion.

In the embodiment of the present invention, the first attachment portion may have a rectangular shape having a predetermined thickness, and a lower surface of the first attachment portion may be fixed to and in close contact with the upper surface of the ingrown fingernail/toenail by a bonding agent.

In the embodiment of the present invention, the first central support portion may include: a first central support member having a roof tile shape protruding upward from the center of the upper surface of the first attachment portion in a direction perpendicular to the first attachment portion; and a first central support member hole formed between the first attachment portion and the first central support member, and a diameter of the first central support member hole may be larger than a diameter of the correction part.

In the embodiment of the present invention, the second fixing part may include: a second attachment portion configured to be attached to the other side of an upper surface of the ingrown fingernail/toenail; and a second central support portion formed at a center of an upper surface of the second attachment portion, and the other side portion of the correction part may be fixedly inserted into the second central support portion.

In the embodiment of the present invention, the second attachment portion may have a rectangular shape having a predetermined thickness, and a lower surface of the second attachment portion may be fixed to and in close contact with the upper surface of the ingrown fingernail/toenail by a bonding agent.

In the embodiment of the present invention, the second central support portion may include: a second central support member having a roof tile shape protruding upward from the center of the upper surface of the second attachment portion in a direction perpendicular to the second attachment portion; and a second central support member hole formed between the second attachment portion and the second central support member, and a diameter of the second central support member hole may be larger than a diameter of the correction part.

In addition, in order to achieve the above-mentioned object, the present invention provides an ingrown fingernail/toenail correction device using a shape memory alloy, the ingrown fingernail/toenail correction device including: a first fixing part configured to be fixed to an ingrown fingernail/toenail; a second fixing part configured to be fixed to the ingrown fingernail/toenail and positioned at the other side of the first fixing part; a third fixing part configured to be fixed to the ingrown fingernail/toenail and positioned between the first fixing part and the second fixing part; and correction parts inserted into the first to third fixing parts and made of a shape memory alloy so that when the correction parts reach a preset temperature, shapes of the correction parts return to preset shapes to provide a corrective force to the first to third fixing parts.

In the embodiment of the present invention, the first fixing part may include: a first attachment portion configured to be attached to one side of an upper surface of the ingrown fingernail/toenail; a first central support portion formed at a center of an upper surface of the first attachment portion; a first one side support portion spaced apart from the first central support portion at a predetermined distance and formed at one side of the upper surface of the first attachment portion; and a first other side support portion spaced apart from the first central support portion at a predetermined distance and formed at the other side of the upper surface of the first attachment portion, and the correction parts may be respectively fixedly inserted into the first central support portion, the first one side support portion, and the first other side support portion.

In the embodiment of the present invention, the first attachment portion may have a rectangular shape having a predetermined thickness, and a lower surface of the first attachment portion may be fixed to and in close contact with the upper surface of the ingrown fingernail/toenail by a bonding agent.

In the embodiment of the present invention, the first central support portion may include: a first central support member having a roof tile shape protruding upward from the center of the upper surface of the first attachment portion in a direction perpendicular to the first attachment portion; and a first central support member hole formed between the first attachment portion and the first central support member, the first one side support portion may include: a first one side support member positioned at one side of the first central support member and having a roof tile shape protruding upward from one side of the upper surface of the first attachment portion in a direction parallel to the first central support member; and a first one side support member hole formed between the first attachment portion and the first one side support member, the first other side support portion may include: a first other side support member positioned at the other side of the first central support member and having a roof tile shape protruding upward from the other side of the upper surface of the first attachment portion in a direction parallel to the first central support member; and a first one side support member hole formed between the first attachment portion and the first other side support member, and a diameter of the first central support member hole, a diameter of the first one side support member hole, and a diameter of the first other side support member hole may be equal to one another and larger than a diameter of the correction part.

In the embodiment of the present invention, the second fixing part may include: a second attachment portion configured to be attached to the other side of the upper surface of the ingrown fingernail/toenail; and a second central support portion formed at a center of an upper surface of the second attachment portion, and the other side portion of the correction part may be fixedly inserted into the second central support portion.

In the embodiment of the present invention, the second attachment portion may have a rectangular shape having a predetermined thickness, and a lower surface of the second attachment portion may be fixed to and in close contact with the upper surface of the ingrown fingernail/toenail by a bonding agent.

In the embodiment of the present invention, the second central support portion may include: a second central support member having a roof tile shape protruding upward from the center of the upper surface of the second attachment portion in a direction perpendicular to the second attachment portion; and a second central support member hole formed between the second attachment portion and the second central support member, and a diameter of the second central support member hole may be larger than a diameter of the correction part.

In the embodiment of the present invention, the third fixing part may include: a third attachment portion configured to be attached to a center of the upper surface of the ingrown fingernail/toenail so as to be positioned between the first attachment portion and the second attachment portion; a third central support portion formed at a center of an upper surface of the third attachment portion; a second one side support portion spaced apart from the third central support portion at a predetermined distance and formed at one side of the upper surface of the third attachment portion; and a second other side support portion spaced apart from the third central support portion at a predetermined distance and formed at the other side of the upper surface of the third attachment portion, and the correction parts may be respectively fixedly inserted into the third central support portion, the second one side support portion, and the second other side support portion.

In the embodiment of the present invention, the third central support portion may include: a third central support member having a roof tile shape protruding upward from the center of the upper surface of the third attachment portion in a direction perpendicular to the third attachment portion; and a third central support member hole formed between the third attachment portion and the third central support member, the second one side support portion may include: a second one side support member positioned at one side of the third central support member and having a roof tile shape protruding upward from one side of the upper surface of the third attachment portion in a direction parallel to the third central support member; and a second one side support member hole formed between the third attachment portion and the second one side support member, the second other side support portion may include: a second other side support member positioned at the other side of the third central support member and having a roof tile shape protruding upward from the other side of the upper surface of the third attachment portion in a direction parallel to the third central support member; and a second one side support member hole formed between the third attachment portion and the second other side support member, and a diameter of the third central support member hole, a diameter of the second one side support member hole, and a diameter of the second other side support member hole may be equal to one another and larger than a diameter of the correction part.

Advantageous Effects

According to the present invention configured as described above, the ingrown fingernail/toenail is corrected by inserting at least one correction part, which is made of a shape memory alloy, into the plurality of fixing parts and then attaching the correction part to the ingrown fingernail/toenail, thereby effectively mitigating a degree of ingrown fingernail/toenail.

The effects of the present invention are not limited to the above-mentioned effects, and it should be understood that the effects of the present invention include all effects that may be derived from the configuration of the present invention disclosed in the detailed description of the present invention or the appended claims.

Figure 4:
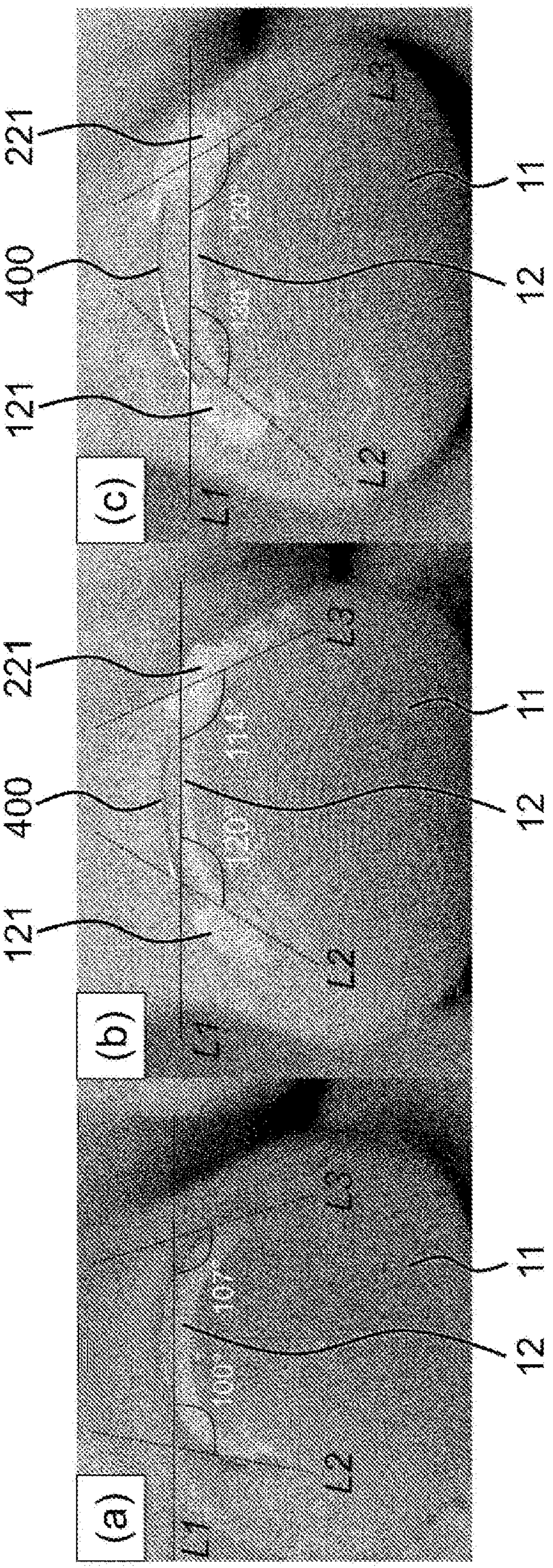

(a), (b), and (c) of FIG. 4 are views illustrating angles of degrees of the ingrown nail in a state in which the ingrown fingernail/toenail correction device using a shape memory alloy according to the first embodiment of the present invention is applied to an ingrown toenail.

Figure 5:
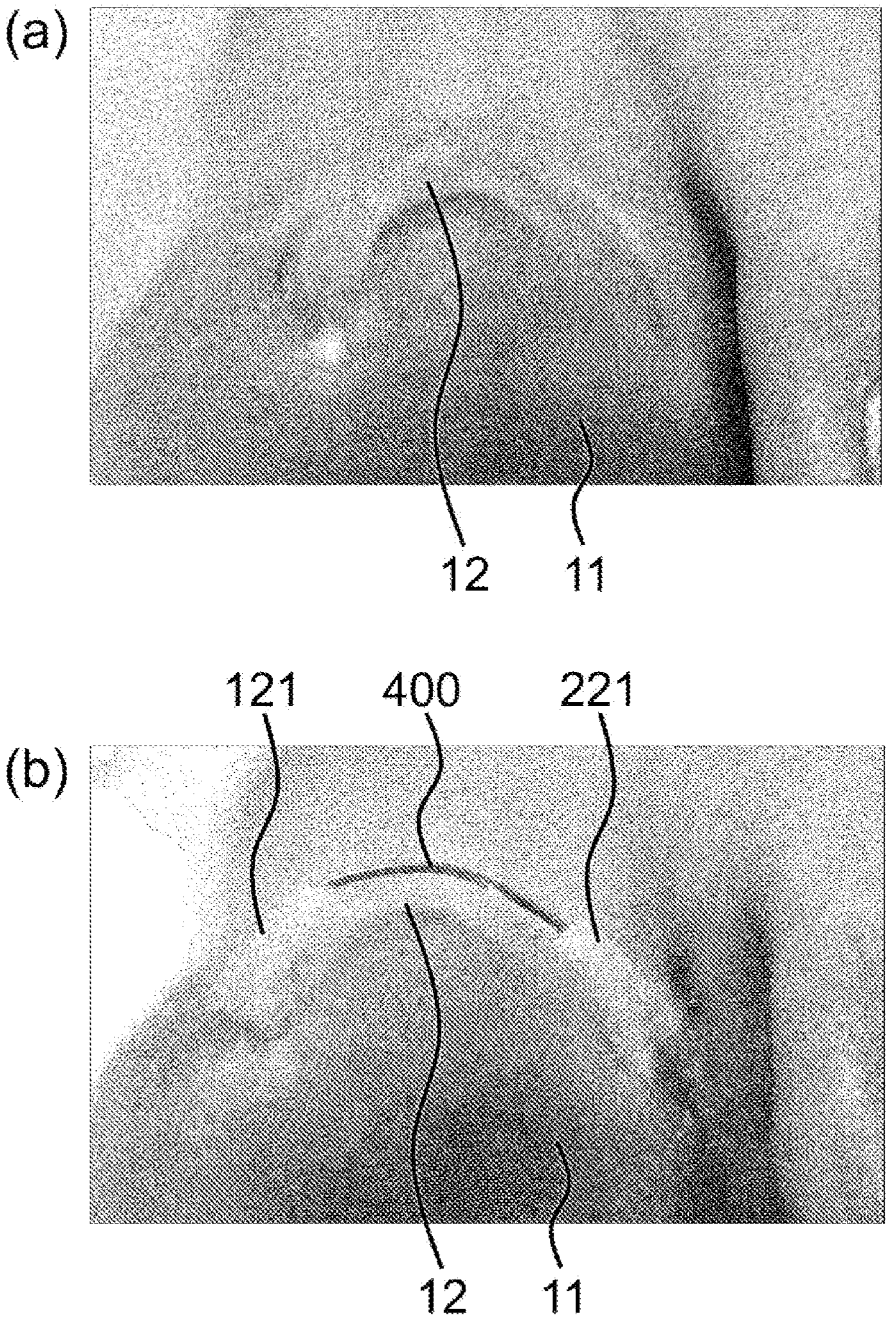

(a) and (b) of FIG. 5 are actual photographs illustrating a state in which the ingrown fingernail/toenail correction device using a shape memory alloy according to the first embodiment of the present invention is applied to patient A.

Figure 6:
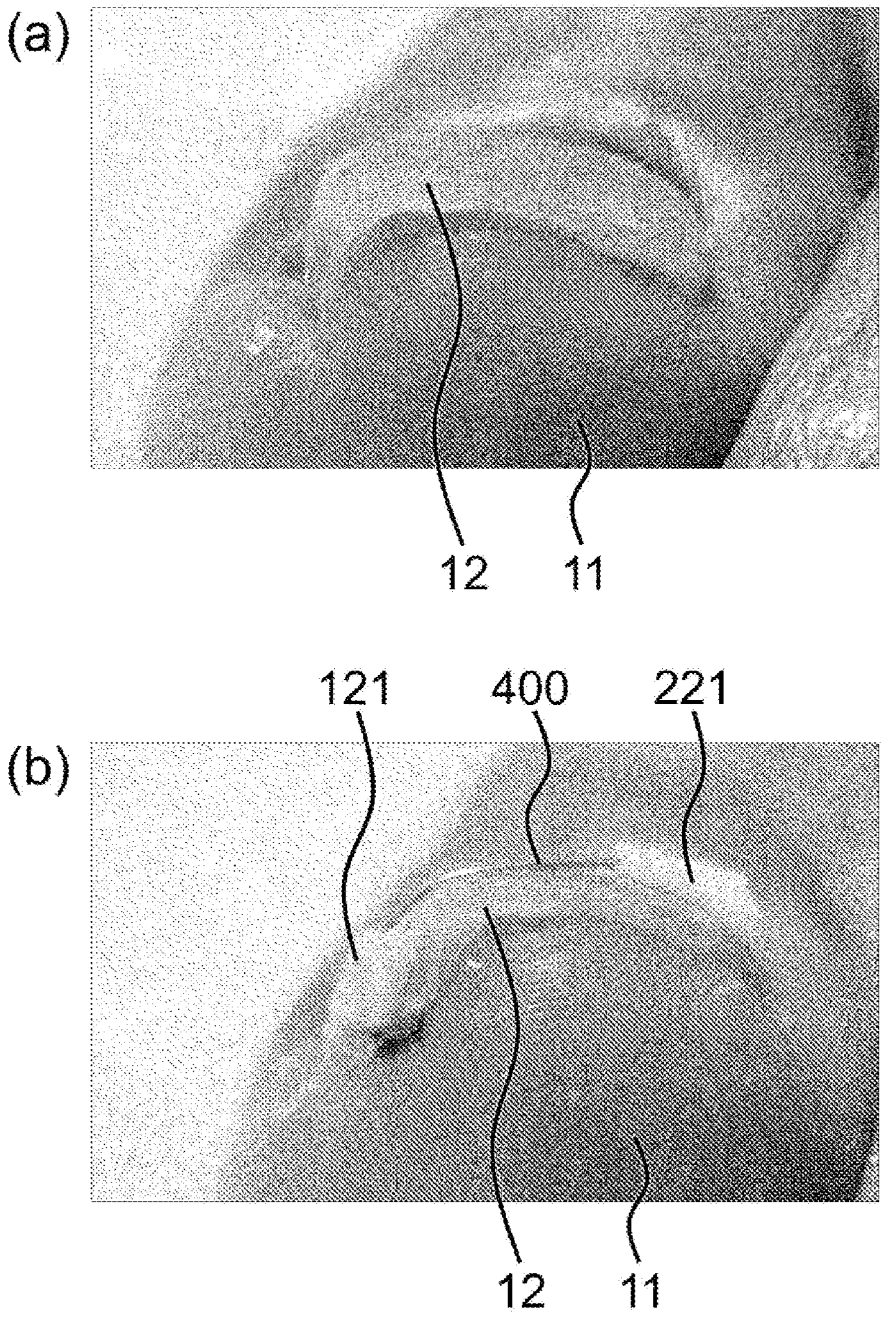

(a) and (b) of FIG. 6 are actual photographs illustrating a state in which the ingrown fingernail/toenail correction device using a shape memory alloy according to the first embodiment of the present invention is applied to patient B.

Figure 7:
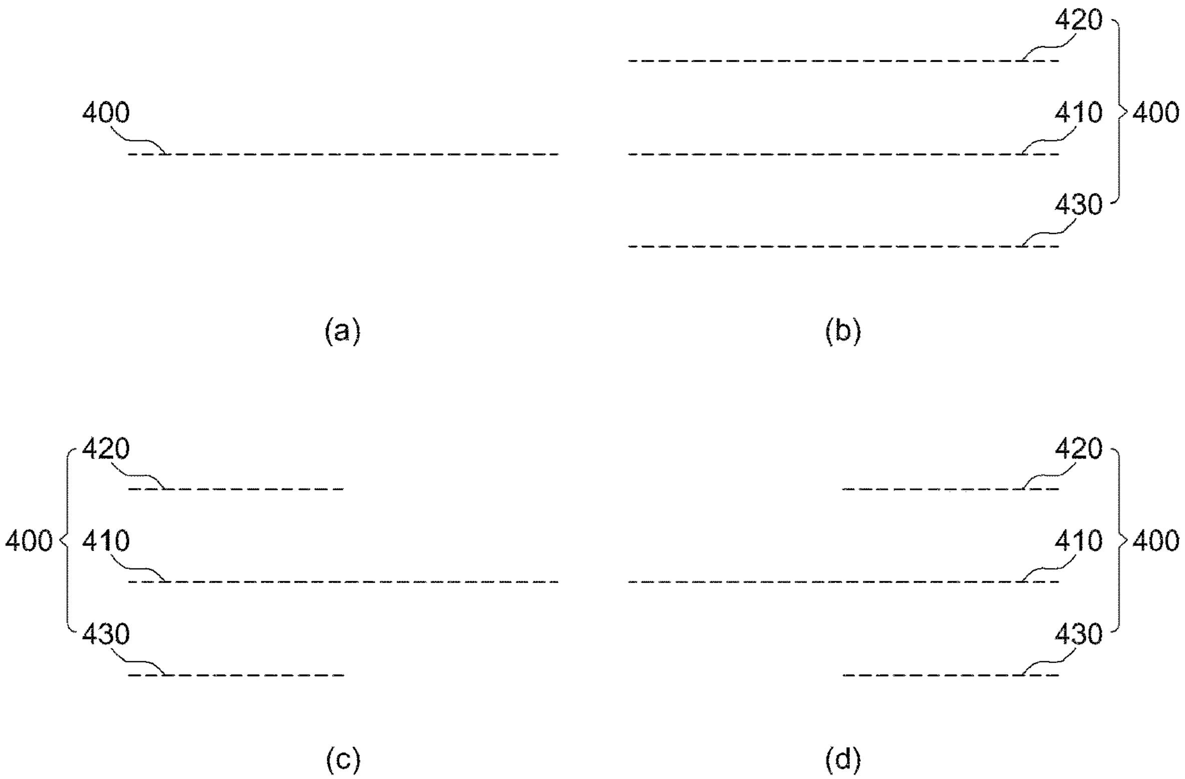

(a), (b), (c), and (d) of FIG. 7 are schematic views illustrating patterns of a correction part applied to the ingrown fingernail/toenail correction device using a shape memory alloy according to the first and second embodiments of the present invention.

Figure 8:
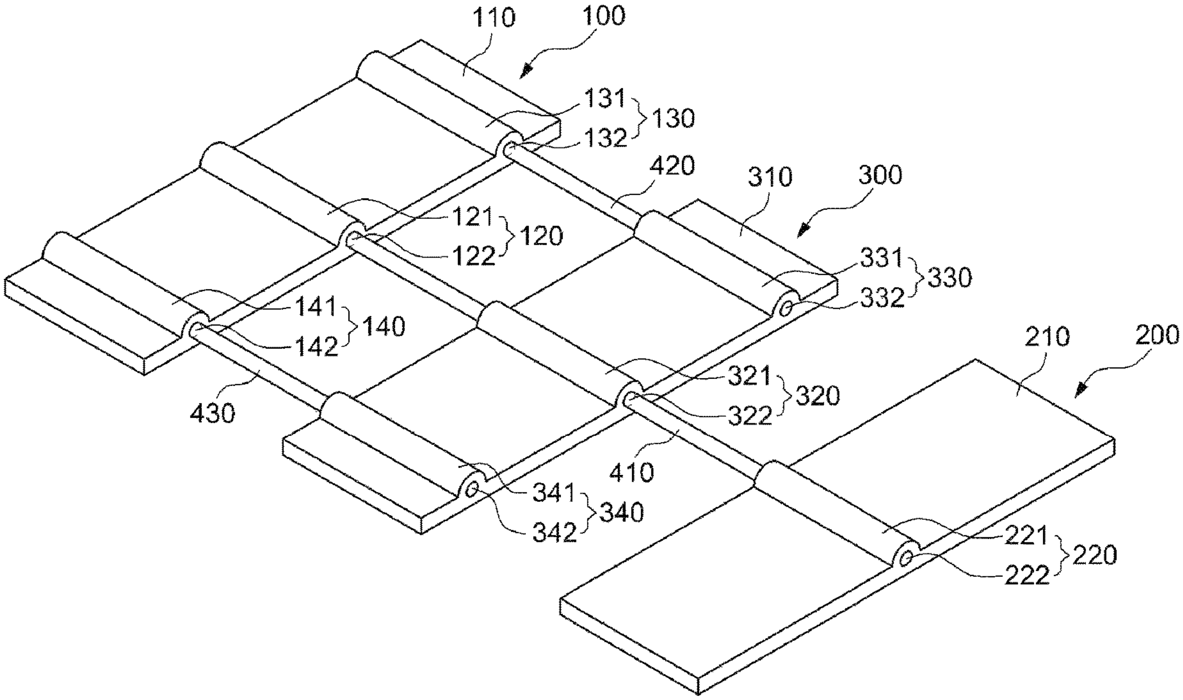

FIG. 8 is a perspective view illustrating an ingrown fingernail/toenail correction device using a shape memory alloy according to a second embodiment of the present invention when viewed in one direction.

Figure 9:
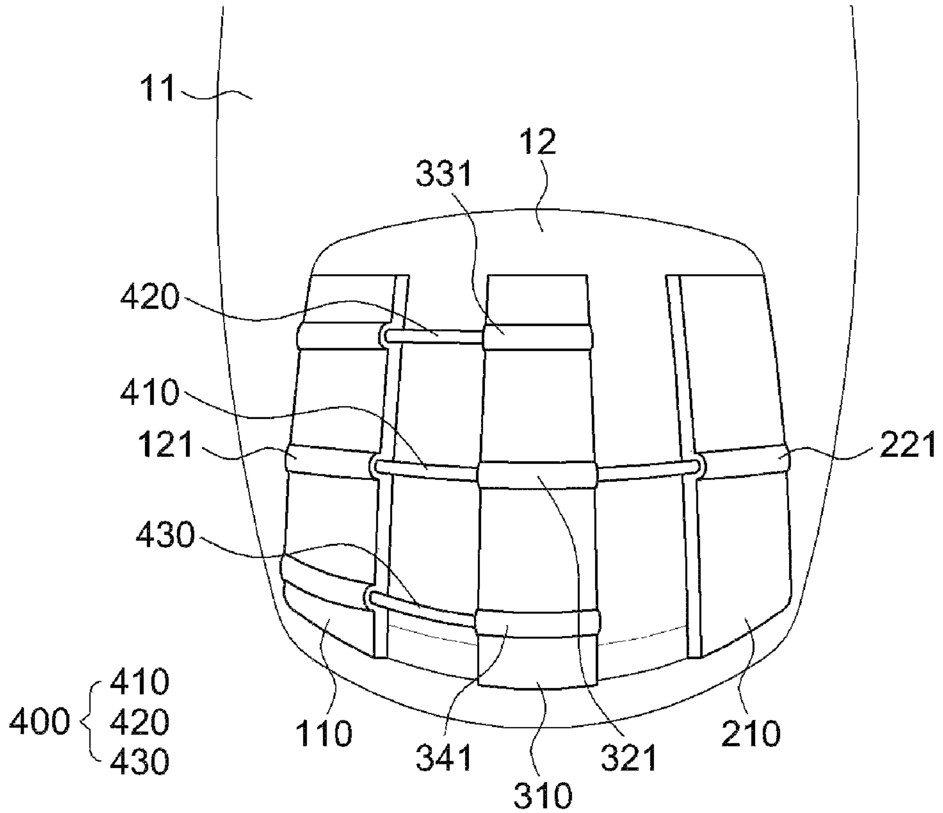

FIG. 9 is a view illustrating a state in which the ingrown fingernail/toenail correction device using a shape memory alloy according to the second embodiment of the present invention is applied to an ingrown fingernail.

BEST MODE

The most exemplary embodiment according to the present invention provides an ingrown fingernail/toenail correction device using a shape memory alloy, the ingrown fingernail/toenail correction device including: a first fixing part configured to be fixed to an ingrown fingernail/toenail; a second fixing part configured to be fixed to the ingrown fingernail/toenail and spaced apart from the first fixing part at a predetermined distance; and a correction part inserted into the first fixing part and the second fixing part and made of a shape memory alloy so that when the correction part reaches a preset temperature, a shape of the correction part returns to a preset shape to provide a corrective force to the first fixing part and the second fixing part.

MODE FOR INVENTION

Hereinafter, the present invention will be described with reference to the accompanying drawings. However, the present invention may be implemented in various different ways and is not limited to the embodiments described herein. Further, a part irrelevant to the description will be omitted in the drawings in order to clearly describe the present invention, and similar constituent elements will be designated by similar reference numerals throughout the specification.

Throughout the present specification, when one constituent element is referred to as being "connected to (coupled to, in contact with, or linked to)" another constituent element, one constituent element can be "directly connected to" the other constituent element, and one constituent element can also be "indirectly connected to" the other element with other elements interposed therebetween. In addition, unless explicitly described to the contrary, the word "comprise/include" and variations such as "comprises/includes" or "comprising/including" will be understood to imply the inclusion of stated elements, not the exclusion of any other elements.

The terms used in the present specification are used only for the purpose of describing particular embodiments and are not intended to limit the present invention. Singular expressions include plural expressions unless clearly described as different meanings in the context. In the present specification, it should be understood the terms "comprises," "comprising," "includes," "including," "containing," "has," "having" or other variations thereof are inclusive and therefore specify the presence of stated features, integers, steps, operations, elements, components, or combinations thereof, but do not preclude the presence or addition of one or more other features, integers, steps, operations, elements, components, or combinations thereof.

Hereinafter, the embodiment of the present invention will be described with reference to the accompanying drawings.

1. First Embodiment: Ingrown Fingernail/Toenail Correction Device (Two Fixing Parts)

Figure 1:
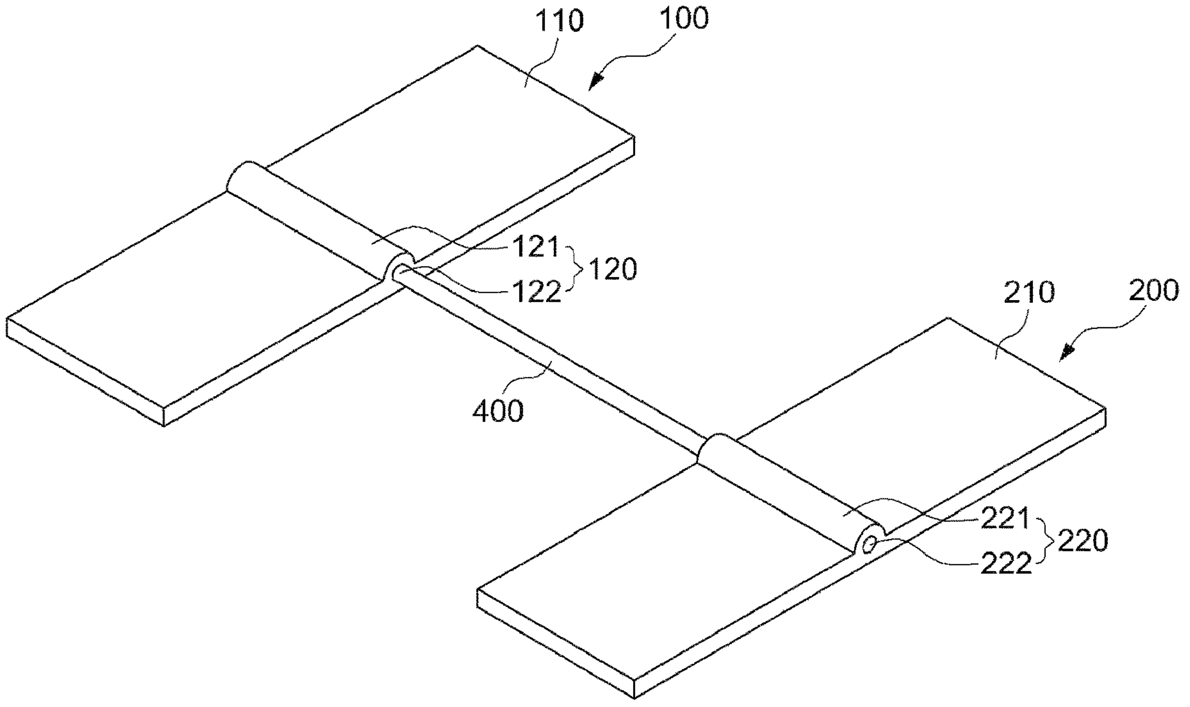
FIG. 1 is a perspective view illustrating an ingrown fingernail/toenail correction device using a shape memory alloy according to a first embodiment of the present invention when viewed in one direction.

FIG. 1 is a perspective view illustrating an ingrown fingernail/toenail correction device using a shape memory alloy according to a first embodiment of the present invention when viewed in one direction.

With reference to FIG. 1, the ingrown fingernail/toenail correction device using a shape memory alloy according to the first embodiment of the present invention includes a first fixing part 100, a second fixing part 200, and a correction part 400.

The first fixing part 100 is fixed to an ingrown fingernail/toenail 12. The first fixing part 100 includes a first attachment portion 110 and a first central support portion 120.

Figure 2:
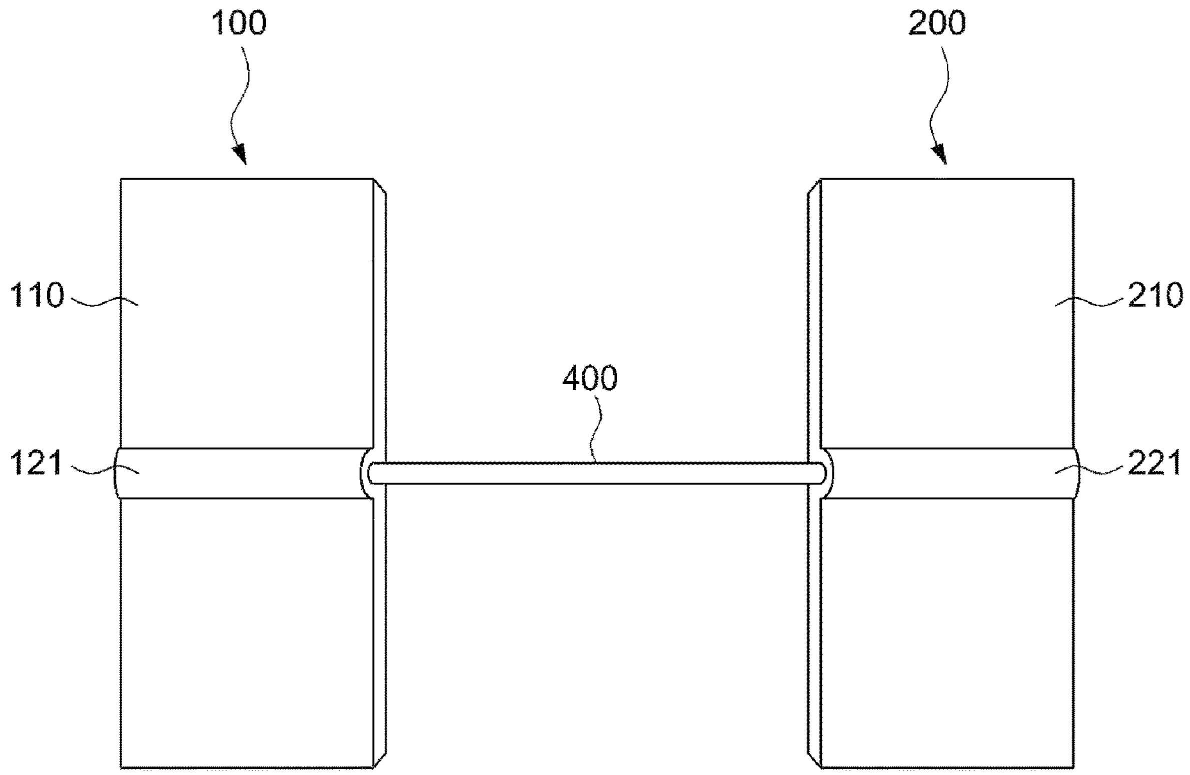
FIG. 2 is a top plan view illustrating the ingrown fingernail/toenail correction device using a shape memory alloy according to the first embodiment of the present invention.
Figure 3:
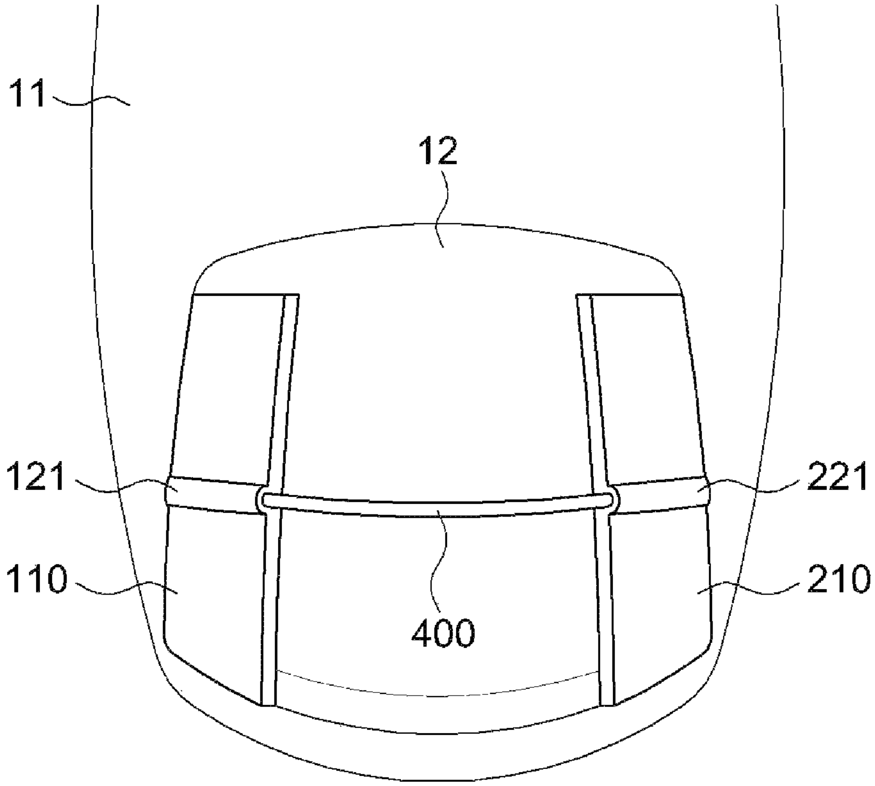
FIG. 3 is an actual photograph illustrating a state in which the ingrown fingernail/toenail correction device using a shape memory alloy according to the first embodiment of the present invention is applied to an ingrown fingernail.

FIG. 2 is a top plan view illustrating the ingrown fingernail/toenail correction device using a shape memory alloy according to the first embodiment of the present invention. FIG. 3 is an actual photograph illustrating a state in which the ingrown fingernail/toenail correction device using a shape memory alloy according to the first embodiment of the present invention is applied to an ingrown fingernail.

With reference to FIGS. 2 and 3, the first attachment portion 110 is attached to one side of an upper surface of the ingrown fingernail/toenail 12. In this case, assuming that a portion of the ingrown fingernail/toenail 12, which is grown and is to be cut, is an upper side of the ingrown fingernail/toenail 12 and a portion positioned opposite to the upper side of the ingrown fingernail/toenail 12 is a lower side of the ingrown fingernail/toenail 12, one side of the upper surface of the ingrown fingernail/toenail 12 corresponds to a left side of based on a line, which connects the upper and lower sides of the ingrown fingernail/toenail 12, and the other side of the upper surface of the ingrown fingernail/toenail 12 corresponds to a right side based on the line that connects the upper and lower sides of the ingrown fingernail/toenail 12.

In addition, the first attachment portion 110 may be made of a rectangular flexible material having a predetermined thickness, for example, flexible plastic. However, the present invention is not limited thereto. For example, in addition to plastic, the first attachment portion 110 may be made of any material, such as tough vinyl or rubber, equivalent to or more flexible than plastic as long as the material may be more appropriately attached and fixed to the ingrown fingernail/toenail 12 by a bonding agent.

A lower surface of the first attachment portion 110 is fixed to and in close contact with the upper surface of the ingrown fingernail/toenail 12 by the bonding agent.

The first central support portion 120 is formed at a center of an upper surface of the first attachment portion 110.

Specifically, a first central support member 121 may have a roof tile shape protruding upward from the center of the upper surface of the first attachment portion 110 in a direction perpendicular to the first attachment portion 110.

More specifically, the first central support member 121 extends to one side and the other side corresponding to a width of the first attachment portion 110.

In addition, the first central support member 121 is also made of a flexible material, like the first attachment portion 110.

A first central support member hole 122 is formed between the first attachment portion 110 and the first central support member 121.

In this case, a diameter of the first central support member hole 122 is larger than a diameter of the correction part 400.

With the above-mentioned structure, one side portion of the correction part 400 is fixedly inserted into the first central support member hole 122.

The second fixing part 200 is spaced apart from the first fixing part 110 at a predetermined distance and fixed to the ingrown fingernail/toenail 12. The second fixing part 200 includes a second attachment portion 210 and a second central support portion 220.

The second attachment portion 210 is attached to the other side of the upper surface of the ingrown fingernail/toenail 12.

In addition, the second attachment portion 210 is made of a rectangular flexible material having a predetermined thickness.

Further, a lower surface of the second attachment portion 210 is fixed to and in close contact with the upper surface of the ingrown fingernail/toenail 12 by the bonding agent.

The second central support portion 220 is formed at a center of an upper surface of the second attachment portion 210. The second central support portion 220 includes a second central support member 221 and a second central support member hole 222.

The second central support member 221 may have a roof tile shape protruding upward from the center of the upper surface of the second attachment portion 210 in a direction perpendicular to the second attachment portion 210. Specifically, the second central support member 221 extends to one side and the other side corresponding to a width of the second attachment portion 210.

The second central support member hole 222 is formed between the second attachment portion 210 and the second central support member 221.

A diameter of the second central support member hole 222 is larger than a diameter of the correction part 400.

With the above-mentioned structure, the other side portion of the correction part 400 is fixedly inserted into the first central support member hole 122.

The first fixing part 100 and the second fixing part 200 may be 3D-printed by using a 3D printer. The first fixing part 100 and the second fixing part 200 may be 3D-printed by any one method among filament extrusion (FDM or FFF), photocurable resin stereolithography (SLA), selective laser sintering (SLS), and ink-jetting (poly-jet).

The correction part 400 may have an annular bar shape, like a wire, and be made of a shape memory alloy.

In this case, the shape memory alloy refers to an alloy having the property (this is called a shape memory effect) that even though the alloy formed in one phase (parent phase) is deformed when the alloy is in another phase, the phase of the alloy is returned to the parent phase, and the shape of the alloy is also returned to the original shape.

For example, once ordinary metal is deformed by a force applied to one end thereof, the shape of the metal is not returned to the original shape only by being heated or cooled. However, some types of alloys have the property that when the alloy is deformed at room temperature, the shape of the alloy is returned to the original shape when the alloy is heated to a predetermined temperature or higher.

One side portion of the correction part 400 is fixedly inserted into the first central support portion 120, and the other side portion of the correction part 400 is fixedly inserted into the second central support portion 220.

Additionally, the present invention may further include tubular corrective force transmission members (not illustrated) inserted into the first central support member 121 through the first central support member hole 122 and inserted into the second central support member 221 through the second central support member hole 222.

The corrective force transmission member may be made of a material having rigidity.

Therefore, one side portion of the correction part 400 is inserted into the corrective force transmission member inserted into the first central support member 121, and the other side portion of the correction part 400 is inserted into the corrective force transmission member inserted into the second central support member 221.

The corrective force transmission members serve to effectively transmit a corrective force provided from the correction part 400 between the first central support portion 120 and two opposite side portions of the correction part 400 and between the second central support portion 220 and two opposite side portions of the correction part 400.

In the absence of the corrective force transmission member, the two opposite side portions of the correction part 400 are in direct contact with the first central support portion 120 and the second central support portion 220, respectively, and the first central support portion 120 and the second central support portion 220 receive the corrective force directly from the two opposite side portions of the correction part 400. For this reason, the first central support portion 120 and the second central support portion 220, which have relatively lower rigidity than the correction part 400, are likely to be physically deformed, and the provided corrective force may not be effectively transmitted.

Therefore, the corrective force transmission members are made of a material having rigidity equal to or higher than the rigidity of the correction part 400 and are in close contact with the inner surface of the first central support portion 120 and the inner surface of the second central support portion 220. Therefore, the contact areas may be increased, thereby minimizing physical deformation of the first and second central support portions 120 and 220 and effectively transmitting the corrective force.

That is, when the correction part 400 is inserted into the first fixing part 110 and the second fixing part 210 and reaches a preset temperature, the shape of the correction part 400 returns to a preset shape, thereby providing the corrective force to the first fixing part 110 and the second fixing part 210.

Specifically, when the temperature reaches the preset temperature in a state in which the correction part 400 has a roof tile shape and a predetermined curvature and one side portion and the other side portion of the correction part 400 are respectively inserted into the first and second central support members 121 and 221, the shape of the correction part 400 returns to a straight shape, i.e., the preset shape, and the corrective force, which is applied upward, is applied to the first fixing part 110 and the second fixing part 210, such that one side and the other side of the ingrown fingernail/toenail 12 of a finger or toe 11 are corrected.

FIGS. 4A, 4B, and 4C are views illustrating angles of degrees of the ingrown nail in a state in which the ingrown fingernail/toenail correction device using a shape memory alloy according to the first embodiment of the present invention is applied to an ingrown toenail.

In FIGS. 4A, 4B, and 4C, a first imaginary line L1 is a tangent line to a center of the upper surface of the ingrown fingernail/toenail 12, a second imaginary line L2 is a tangent line to the other side of the ingrown fingernail/toenail 12, and a third imaginary line L3 is a tangent line to one side of the ingrown fingernail/toenail 12.

In this case, an angle between the first imaginary line L1 and the second imaginary line L2 and an angle between the first imaginary line L1 and the third imaginary line L3 are measures for determining a degree of the ingrown fingernail/toenail.

FIG. 4A is a view illustrating that the ingrown toenail 12 is in a severe state. As illustrated in FIG. 4A, it can be ascertained that the angle between the first imaginary line L1 and the second imaginary line L2 is 100°, and the angle between the first imaginary line L1 and the second imaginary line L2 is 107°.

Next, FIG. 4B illustrates a change after the present invention is applied to the ingrown toenail 12 after the state in FIG. 4A. As illustrated in FIG. 4B, it can be ascertained that the angle between the first imaginary line L1 and the second imaginary line L2 is 120°, the angle between the first imaginary line L1 and the second imaginary line L2 is 114°, and the degree of the ingrown nail is improved in comparison with the ingrown toenail 12 illustrated in FIG. 4A.

Next, FIG. 4C illustrates that the ingrown toenail 12 is finally corrected by the present invention after the state in FIG. 4B. As illustrated in FIG. 4C, it can be ascertained that the angle between the first imaginary line L1 and the second imaginary line L2 is 130°, the angle between the first imaginary line L1 and the second imaginary line L2 is 120°, and the degree of the ingrown nail is improved as the ingrown toenail 12 is further corrected in comparison with the ingrown toenails 12 illustrated in FIGS. 4A and 4B.

FIGS. 5A and 5B are actual photographs illustrating a state in which the ingrown fingernail/toenail correction device using a shape memory alloy according to the first embodiment of the present invention is applied to patient A.

FIG. 5A illustrates the ingrown toenail 12 of patient A, and FIG. 5B illustrates that the ingrown toenail 12 is corrected after the present invention is applied to the ingrown toenail 12 of patient A.

FIGS. 6A and 5B are actual photographs illustrating a state in which the ingrown fingernail/toenail correction device using a shape memory alloy according to the first embodiment of the present invention is applied to patient B.

FIG. 6A illustrates the ingrown toenail 12 of patient B, and FIG. 6B illustrates that the ingrown toenail 12 is corrected after the present invention is applied to the ingrown toenail 12 of patient B.

As illustrated in FIGS. 5 and 6, it can be ascertained that when the present invention is applied to the ingrown fingernail/toenail 12, the degree of the ingrown nail is improved in comparison with the state made before the present invention is applied, and it can be ascertained that the present invention is effective in correcting the ingrown fingernail/toenail 12.

FIGS. 7A, 7B, 7C, and 7D are schematic views illustrating patterns of the correction part applied to the ingrown fingernail/toenail correction device using a shape memory alloy according to the first and second embodiments of the present invention.

In the first embodiment of the present invention, the correction part 400 is applied, as illustrated in FIG. 7A.

However, as a modified embodiment, a first one side support portion and a first other side support portion, which are identical in shape to the first central support portion 120, may be formed at two opposite sides of the upper surface of the first attachment portion 110 so as to be spaced apart from the first central support portion 120, which is formed on the first attachment portion 110, at a predetermined distance, and a second one side support portion and a second other side support portion, which are identical in shape to the second central support portion 220, may be formed at two opposite sides of the upper surface of the second attachment portion 210 so as to be spaced apart from the second central support portion 220, which is formed on the second attachment portion 210, at a predetermined distance.

As illustrated in FIG. 7B, in the modified embodiment, the correction part 400 including a first correction member 410, a second correction member 420, and a third correction member 430 may be applied.

2. Second Embodiment: Ingrown Fingernail/Toenail Correction Device (Three Fixing Parts)

Hereinafter, an ingrown fingernail/toenail correction device using a shape memory alloy according to a second embodiment of the present invention will be described with reference to FIGS. 1 to 9.

FIG. 8 is a perspective view illustrating the ingrown fingernail/toenail correction device using a shape memory alloy according to the second embodiment of the present invention when viewed in one direction.

With reference to FIG. 8, the ingrown fingernail/toenail correction device using a shape memory alloy according to the second embodiment of the present invention includes the first fixing part 100, the second fixing part 200, a third fixing part 300, and the correction part 400.

The first fixing part 100 may be fixed to the ingrown fingernail/toenail 12 and made of a flexible material.

To this end, the first fixing part 100 includes the first attachment portion 110, the first central support portion 120, a first one side support portion 130, and a first other side support portion 140.

FIG. 9 is a view illustrating a state in which the ingrown fingernail/toenail correction device using a shape memory alloy according to the second embodiment of the present invention is applied to an ingrown fingernail.

With reference to FIG. 9, the first attachment portion 110 is attached to one side of the upper surface of the ingrown fingernail/toenail 12.

Specifically, the first attachment portion 110 is made of a rectangular flexible material having a predetermined thickness.

In addition, the lower surface of the first attachment portion 110 is fixed to and in close contact with the upper surface of the ingrown fingernail/toenail 12 by the bonding agent.

The first central support portion 120 is formed at the center of the upper surface of the first attachment portion 110 and identical to the first central support portion 120 according to the first embodiment.

The first central support portion 120 includes the first central support member 121 and the first central support member hole 122.

The first central support member 121 has a roof tile shape protruding upward from the center of the upper surface of the first attachment portion 110 in the direction perpendicular to the first attachment portion 110.

The first central support member hole 122 is formed between the first attachment portion 110 and the first central support member 121.

The first one side support portion 130 is spaced apart from the first central support portion 120 at a predetermined distance and formed at one side of the upper surface of the first attachment portion 110.

The first one side support portion 130 includes a first one side support member 131 and a first one side support member hole 132.

The first one side support member 131 is positioned at one side of the first central support member 121 and has a roof tile shape protruding upward from one side of the upper surface of the first attachment portion 110 in a direction parallel to the first central support member 121.

The first one side support member hole 132 is formed between the first attachment portion 110 and the first one side support member 131.

The first other side support portion 140 is spaced apart from the first central support portion 120 at a predetermined distance and formed at the other side of the upper surface of the first attachment portion 110.

The first other side support portion 140 includes a first other side support member 141 and a first other side support member hole 142.

The first other side support member 141 is positioned at the other side of the first central support member 121 and has a roof tile shape protruding upward from the other side of the upper surface of the first attachment portion 110 in a direction parallel to the first central support member 121.

The first other side support member hole 142 is formed between the first attachment portion 110 and the first other side support member 141.

The first central support portion 120, the first one side support portion 130, and the first other side support portion 140 are identical in shape and structure to one another, and positions at which the first central support portion 120, the first one side support portion 130, and the first other side support portion 140 are formed on the first attachment portion 110 are different from one another.

In addition, a diameter of the first central support member hole 122, a diameter of the first one side support member hole 132, and a diameter of the first other side support member hole 142 are equal to one another and larger than a diameter of each of the first to third correction members 410, 420, and 430.

The second fixing part 200 is positioned at the other side of the first fixing part 110 and fixed to the ingrown fingernail/toenail 120. In addition, the second fixing part 200 may also be made of a flexible material.

The second fixing part 200 includes the second attachment portion 210 and the second central support portion 220.

As illustrated in FIG. 9, the second attachment portion 210 is attached to the other side of the upper surface of the ingrown fingernail/toenail 12.

In addition, as illustrated in FIG. 8, the second attachment portion 210 is made of a rectangular flexible material having a predetermined thickness.

Further, the lower surface of the second attachment portion 210 is fixed to and in close contact with the upper surface of the ingrown fingernail/toenail 12 by the bonding agent.

The second central support portion 220 is formed at the center of the upper surface of the second attachment portion 210.

The second central support portion 220 includes the second central support member 221 and the second central support member hole 222.

The second central support member 221 has a roof tile shape protruding upward from the center of the upper surface of the second attachment portion 210 in the direction perpendicular to the second attachment portion 210.

The second central support member hole 222 is formed between the second attachment portion 210 and the second central support member 221.

A diameter of the second central support member hole 222 is larger than the diameter of each of the first to third correction members 410, 420, and 430.

The third fixing part 300 is positioned between the first fixing part 110 and the second fixing part 210 and fixed to the ingrown fingernail/toenail 120. In addition, the third fixing part 300 may also be made of a flexible material.

The third fixing part 300 includes a third attachment portion 310, a third central support portion 320, a second one side support portion 330, and a second other side support portion 340.

The third attachment portion 310 is attached to the center of the upper surface of the ingrown fingernail/toenail 12 so as to be positioned between the first attachment portion 110 and the second attachment portion 210.

The third central support portion 320 is formed at a center of an upper surface of the third attachment portion 310.

The third central support portion 320 includes a third central support member 321 and a third central support member hole 322.

The third central support member 321 has a roof tile shape protruding upward from the center of the upper surface the third attachment portion 310 in a direction perpendicular to the third attachment portion 310.

The third central support member hole 322 is formed between the third attachment portion 310 and the third central support member 321.

The second one side support portion 330 is spaced apart from the third central support portion 320 at a predetermined distance and formed at one side of the upper surface of the third attachment portion 310.

The second one side support portion 330 includes a second one side support member 331 and a second one side support member hole 332.

The second one side support member 331 is positioned at one side of the third central support member 321 and protrudes upward from one side of the upper surface of the third attachment portion 310 in a direction parallel to the third central support member 321.

The second one side support member hole 332 is formed between the third attachment portion 310 and the second one side support member 331.

The second other side support portion 340 is spaced apart from the third central support portion 320 at a predetermined distance and formed at the other side of the upper surface of the third attachment portion 310.

The second other side support portion 340 includes a second other side support member 341 and a second other side support member hole 342.

The second other side support member 341 is positioned at the other side of the third central support member 321 and has a roof tile shape protruding upward from the other side of the upper surface of the third attachment portion 310 in the direction parallel to the third central support member 321.

The second other side support member hole 342 is formed between the third attachment portion 310 and the second other side support member 341.

A diameter of the third central support member hole 322, a diameter of the second one side support member hole 332, and a diameter of the second other side support member hole 342 are equal to one another and larger than the diameter of each of the first to third correction members 410, 420, and 430.

Therefore, the first to third correction members 410, 420, and 430 are respectively fixedly inserted into the third central support portion 320, the second one side support portion 330, and the second other side support portion 340.

The first fixing part 100, the second fixing part 200, and the third fixing part 300 may be 3D-printed by using a 3D printer. The first fixing part 100, the second fixing part 200, and the third fixing part 300 may be 3D-printed by any one method among filament extrusion (FDM or FFF), photocurable resin stereolithography (SLA), selective laser sintering (SLS), and ink-jetting (poly-jet).

The correction parts 400 may be made of a shape memory alloy, such that when the correction parts 400 are inserted into the first to third fixing parts 110, 210, and 310 and reach a preset temperature, the shapes of the correction parts 400 return to preset shapes, thereby providing the corrective force to the first to third fixing parts 110, 210, and 310.

The correction parts 400 include the first correction member 410, the second correction member 420, and the third correction member 430.

The first correction member 410, the second correction member 420, and the third correction member 430 may each have an annular bar shape and extend by a predetermined distance, like a wire.

However, the second correction member 420 and the third correction member 430 are equal in length to each other, and the first correction member 410 is longer than the second correction member 420 and the third correction member 430.

With reference to FIG. 7C, the first to third correction members 410, 420, and 430 are respectively fixedly inserted into the first central support portion 120, the first one side support portion 130, and the first other side support portion 140.

The first correction member 410 is fixedly inserted into the second central support portion 220.

Specifically, as illustrated in FIG. 8, a central portion of the first correction member 410 passes through the third central support member hole 322 and is positioned in the third central support member 321.

In addition, as illustrated in FIG. 8, one side portion of the first correction member 410 passes through the first central support member hole 122 and is positioned in the first central support member 121.

In addition, as illustrated in FIG. 8, the other side portion of the first correction member 410 passes through the second central support member hole 222 and is positioned in the second central support member 221.

As illustrated in FIG. 8, one side portion of the first correction member 410 passes through the first one side support member hole 132 and is positioned in the first one side support member 131.

As illustrated in FIG. 8, the other side portion of the second correction member 420 passes through the second one side support member hole 332 and is positioned in the second one side support member 331.

As illustrated in FIG. 8, one side portion of the third correction member 430 passes through the first other side support member hole 142 and is positioned in the first other side support member 141.

As illustrated in FIG. 8, the other side portion of the third correction member 430 passes through the second other side support member hole 342 and positioned in the second other side support member 341.

Meanwhile, as illustrated in FIGS. 7B and 7D, the present invention may be implemented in accordance with the presence or absence of the first one side support portion 130, the first other side support portion 140, the second one side support portion 230, and the second other side support portion 240.

The configuration in FIG. 7B may be implemented when one side support portion (not illustrated), which is identical in shape to the first one side support portion 130, is formed on the second attachment portion 210 at the same position as the first one side support portion 130, and the other side support portion (not illustrated), which is identical in shape to the first other side support portion 140, is formed on the second attachment portion 210 at the same position as the second other side support portion 140 in the state illustrated in FIG. 8.

Meanwhile, the configuration in FIG. 7 may be implemented when the first one side support portion 130 and the first other side support portion 140 are not provided, and the other side support portion (not illustrated), which is identical in shape to the first other side support portion 140, is formed on the second attachment portion 210 at the same position as the second other side support portion 140 in the state illustrated in FIG. 8.

It will be appreciated that the embodiments of the present invention have been described above for purposes of illustration, and those skilled in the art may understand that the present invention may be easily modified in other specific forms without changing the technical spirit or the essential features of the present invention. Therefore, it should be understood that the above-described embodiments are illustrative in all aspects and do not limit the present invention. For example, each component described as a single type may be carried out in a distributed manner. Likewise, components described as a distributed type can be carried out in a combined type.

The scope of the present invention is represented by the claims to be described below, and it should be interpreted that the meaning and scope of the claims and all the changes or modified forms derived from the equivalent concepts thereto fall within the scope of the present invention.

DESCRIPTION OF REFERENCE NUMERALS

100: First fixing part
110: First attachment portion
120: First central support portion
121: First central support member
122: First central support member hole
130: First one side support portion
131: First one side support member
132: First one side support member hole
140: First other side support portion
141: First other side support member
142: First other side support member hole
200: Second fixing part
210: Second attachment portion
220: Second central support portion
300: Third fixing part
310: Third attachment portion
320: Third central support portion
321: Third central support member
322: Third central support member hole
330: Second one side support portion
331: Second one side support member
332: Second one side support member hole
340: Second other side support portion
341: Second other side support member
342: Second other side support member hole
400: Correction part
410: First correction member
420: Second correction member
430: Third correction member

The invention claimed is:

1. An ingrown fingernail/toenail correction device using a shape memory alloy, the ingrown fingernail/toenail correction device comprising:

a first fixing part configured to be fixed to an ingrown fingernail/toenail;

a second fixing part configured to be fixed to the ingrown fingernail/toenail and positioned at a side of the first fixing part;

a third fixing part configured to be fixed to the ingrown fingernail/toenail and positioned between the first fixing part and the second fixing part; and correction parts configured to be inserted into the first to third fixing parts and made of a shape memory alloy to ensure that when the correction parts reach a preset temperature, shapes of the correction parts return to preset shapes to provide a corrective force to the first to third fixing parts.

2. The ingrown fingernail/toenail correction device of claim 1, wherein the first fixing part comprises:

a first attachment portion configured to be attached to one side of an upper surface of the ingrown fingernail/toenail;

a first central support portion defined at a center of an upper surface of the first attachment portion;

a first one side support portion spaced apart from the first central support portion at a predetermined distance and defined at one side of the upper surface of the first attachment portion; and a first other side support portion spaced apart from the first central support portion at a predetermined distance and defined at another side of the upper surface of the first attachment portion, and wherein each of the correction parts is respectively and fixedly inserted into the first central support portion, the first one side support portion, and the first other side support portion.

3. The ingrown fingernail/toenail correction device of claim 2, wherein the third fixing part comprises:

a third attachment portion configured to be attached to a center of the upper surface of the ingrown fingernail/toenail and positioned between the first attachment portion and a second attachment portion;

a third central support portion defined at a center of an upper surface of the third attachment portion;

a second one side support portion spaced apart from the third central support portion at a predetermined distance and defined at one side of the upper surface of the third attachment portion; and a second other side support portion spaced apart from the third central support portion at a predetermined distance and defined at another side of the upper surface of the third attachment portion, and wherein each of the correction parts is respectively and fixedly inserted into the third central support portion, the second one side support portion, and the second other side support portion.

4. The ingrown fingernail/toenail correction device of claim 3, wherein the third central support portion comprises:

a third central support member having a roof tile shape protruding upward from the center of the upper surface of the third attachment portion in a direction perpendicular to the third attachment portion; and a third central support member hole defined between the third attachment portion and the third central support member, wherein the second one side support portion comprises:

a second one side support member positioned at one side of the third central support member and having a roof tile shape protruding upward from one side of the upper surface of the third attachment portion in a direction parallel to the third central support member; and a second one side support member hole defined between the third attachment portion and the second one side support member, wherein the second other side support portion comprises:

a second other side support member positioned at another side of the third central support member and having a roof tile shape protruding upward from another side of the upper surface of the third attachment portion in a direction parallel to the third central support member; and a second other side support member hole defined between the third attachment portion and the second other side support member, and wherein a diameter of the third central support member hole, a diameter of the second one side support member hole, and a diameter of the second other side support member hole are equal to one another and larger than a diameter of each of the correction parts.

5. The ingrown fingernail/toenail correction device of claim 2, wherein the first attachment portion has a rectangular shape having a predetermined thickness, and a lower surface of the first attachment portion is fixed to and in close contact with the upper surface of the ingrown fingernail/toenail by a bonding agent.

6. The ingrown fingernail/toenail correction device of claim 2, wherein the first central support portion comprises:

a first central support member having a roof tile shape protruding upward from the center of the upper surface of the first attachment portion in a direction perpendicular to the first attachment portion; and a first central support member hole defined between the first attachment portion and the first central support member, wherein the first one side support portion comprises:

a first one side support member positioned at one side of the first central support member and having a roof tile shape protruding upward from one side of the upper surface of the first attachment portion in a direction parallel to the first central support member; and a first one side support member hole defined between the first attachment portion and the first one side support member, wherein the first other side support portion comprises:

a first other side support member positioned at another side of the first central support member and having a roof tile shape protruding upward from another side of the upper surface of the first attachment portion in a direction parallel to the first central support member; and a first one side support member hole defined between the first attachment portion and the first other side support member, and wherein a diameter of the first central support member hole, a diameter of the first one side support member hole, and a diameter of a first other side support member hole are equal to one another and larger than a diameter of each of the correction parts.

7. The ingrown fingernail/toenail correction device of claim 1, wherein the second fixing part comprises:

a second attachment portion configured to be attached to one side of an upper surface of the ingrown fingernail/toenail; and a second central support portion defined at a center of an upper surface of the second attachment portion, and wherein one side portion of one of the correction parts is fixedly inserted into the second central support portion.

8. The ingrown fingernail/toenail correction device of claim 7, wherein the second attachment portion has a rectangular shape having a predetermined thickness, and a lower surface of the second attachment portion is fixed to and in close contact with the upper surface of the ingrown fingernail/toenail by a bonding agent.

9. The ingrown fingernail/toenail correction device of claim 7, wherein the second central support portion comprises:

a second central support member having a roof tile shape protruding upward from the center of the upper surface of the second attachment portion in a direction perpendicular to the second attachment portion; and a second central support member hole defined between the second attachment portion and the second central support member, and wherein a diameter of the second central support member hole is larger than a diameter of one of the correction parts.

10. An ingrown fingernail/toenail correction device using a shape memory alloy, the ingrown fingernail/toenail correction device comprising:

a first fixing part configured to be fixed to an ingrown fingernail/toenail;

a second fixing part configured to be fixed to the ingrown fingernail/toenail and spaced apart from the first fixing part at a predetermined distance; and a correction part configured to be inserted into the first fixing part and the second fixing part and made of a shape memory alloy to ensure that when the correction part reaches a preset temperature, a shape of the correction part returns to a preset shape to provide a corrective force to the first fixing part and the second fixing part, wherein the first fixing part comprises:

a first attachment portion configured to be attached to one side of an upper surface of the ingrown fingernail/toenail; and a first central support portion defined at a center of an upper surface of the first attachment portion, wherein one side portion of the correction part is fixedly inserted into the first central support portion, wherein the first central support portion comprises:

a first central support member having a roof tile shape protruding upward from the center of the upper surface of the first attachment portion in a direction perpendicular to the first attachment portion; and a first central support member hole defined between the first attachment portion and the first central support member, and wherein a diameter of the first central support member hole is larger than a diameter of the correction part.

11. The ingrown fingernail/toenail correction device of claim 1, wherein the second fixing part comprises:

a second attachment portion configured to be attached to another side of the upper surface of the ingrown fingernail/toenail; and a second central support portion defined at a center of an upper surface of the second attachment portion, and wherein another side portion of the correction part is fixedly inserted into the second central support portion.

12. The ingrown fingernail/toenail correction device of claim 11, wherein the second attachment portion has a rectangular shape having a predetermined thickness, and a lower surface of the second attachment portion is fixed to and in close contact with the upper surface of the ingrown fingernail/toenail by a bonding agent.

13. The ingrown fingernail/toenail correction device of claim 11, wherein the second central support portion comprises:

a second central support member having a roof tile shape protruding upward from the center of the upper surface of the second attachment portion in a direction perpendicular to the second attachment portion; and a second central support member hole defined between the second attachment portion and the second central support member, and wherein a diameter of the second central support member hole is larger than the diameter of the correction part.

14. The ingrown fingernail/toenail correction device of claim 1, wherein the first attachment portion has a rectangular shape having a predetermined thickness, and a lower surface of the first attachment portion is fixed to and in close contact with the upper surface of the ingrown fingernail/toenail by a bonding agent.

* * * * *